United States Patent
Gai et al.

(10) Patent No.: US 11,220,681 B2
(45) Date of Patent: Jan. 11, 2022

(54) ENZYMATIC REACTION MEDIUM CONTAINING SURFACTANT

(71) Applicant: Novartis AG, Basel (CH)

(72) Inventors: Yu Gai, Jiangsu (CN); Fabrice Gallou, Basel (CH); Feng Gao, Jiangsu (CN); Pengfei Guo, Jiangsu (CN); Weiyong Kong, Jiangsu (CN); Michael Parmentier, Basel (CH); Jianguang Zhou, Suzhou (CN)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/478,149

(22) PCT Filed: Jan. 11, 2018

(86) PCT No.: PCT/IB2018/050179
§ 371 (c)(1),
(2) Date: Jul. 16, 2019

(87) PCT Pub. No.: WO2018/134710
PCT Pub. Date: Jul. 26, 2018

(65) Prior Publication Data
US 2019/0367900 A1 Dec. 5, 2019

(30) Foreign Application Priority Data
Jan. 19, 2017 (WO) ................ PCT/CN2017/071668

(51) Int. Cl.
| | |
|---|---|
| *C12N 9/96* | (2006.01) |
| *C12P 7/22* | (2006.01) |
| *C12N 9/04* | (2006.01) |
| *C12N 9/02* | (2006.01) |
| *C12P 17/06* | (2006.01) |
| *C12P 17/12* | (2006.01) |

(52) U.S. Cl.
CPC ............... *C12N 9/96* (2013.01); *C12N 9/001* (2013.01); *C12N 9/0006* (2013.01); *C12P 7/22* (2013.01); *C12P 17/06* (2013.01); *C12P 17/12* (2013.01)

(58) Field of Classification Search
CPC ........ C12N 9/96; C12N 9/0006; C12N 9/001; C12P 17/12; C12P 17/06; C12P 7/22; C11D 3/38663
See application file for complete search history.

(56) References Cited

U.S. PATENT DOCUMENTS

2014/0329734 A1    11/2014   Pegelow et al.

OTHER PUBLICATIONS

Stephen Wallace et al., "Designer Micelles Accelerate Flux Through Engineered Metabolism in *E. coli* and Support Biocompatible Chemistry", Angewandte Chemie International Edition, vol. 55, No. 20, pp. 6023-6027, Apr. 8, 2016.
Stephen Wallace et al., "Designer Micelles Accelerate Flux Through Engineered Metabolism in *E-coli* and Support Biocompatible Chemistry, Supporting Information", Angewandte Chemie, Apr. 2016 (Apr. 2016), pp. 1-24, Retrieved from the Internet: URL:anie201600966-sup-0001-misc information.pdf, [retrieved on Apr. 10, 2018].
Fabrice Gallou et al., "Surfactant technology applied toward an active pharmaceutical ingredient: more than a simple green chemistry advance", Green Chemistry, vol. 18, No. 1, pp. 14-19, 2016.
Christiansen, A., et al.,"Effects of non-ionic surfactants on cytochrome P450-mediated metabolism in vitro", European Journal of Pharmaceutics and Biopharmaceutics, V.78(1), pp. 166-172, (2011,).
Stephanopoulos, G., "Metabolic Fluxes and Metabolic Engineering", Metabolic Engineering, vol. 1, pp. 1-11, (1999).

*Primary Examiner* — Satyendra K Singh
(74) *Attorney, Agent, or Firm* — Francine F. Li

(57) ABSTRACT

The present invention is directed to aqueous reaction mixtures for enzymatic synthesis reactions comprising a surfactant. The surfactant in the reaction mixture increases stability and yield of the enzymatic reaction. Furthermore, method for performing an enzymatic reaction using said aqueous reaction mixtures are provided.

39 Claims, No Drawings

ENZYMATIC REACTION MEDIUM CONTAINING SURFACTANT

FIELD OF THE INVENTION

The present invention is directed to improved reaction media for enzymatic synthesis reactions. The reaction medium comprises a specific surfactant which enhances solvation of the reactants and products of the chemical reaction and increases the activity of the enzyme compared to conventional surfactants. The use of the specific surfactant leads to an improved yield and a more robust enzymatic reaction. The invention therefore provides a reaction mixture comprising an enzyme and a surfactant and a method of performing an enzymatic reaction using said reaction mixture.

BACKGROUND OF THE INVENTION

New catalytic synthetic methods in organic chemistry that satisfy increasingly stringent environmental constraints are in great demand by the pharmaceutical and chemical industries. In addition, novel catalytic procedures are necessary to produce the emerging classes of organic compounds that are becoming the targets of molecular and biomedical research. Enzyme-catalyzed chemical transformations are now widely recognized as practical alternatives to traditional (non-biological) organic synthesis, and as convenient solutions to certain intractable synthetic problems.

Enzymatic reactions are generally performed in aqueous media. However, many substrates and products of interest in the synthetic chemical industry are hydrophobic and only partially water-soluble. To improve solubility, often organic solvents are added to the reaction mixture. These organic solvents, on the other hand, are detrimental for the stability and performance of many enzymes. Furthermore, several organic solvents are harmful for the environment.

Hence, there is a need in the art to provide a reaction media for enzymatic synthesis reactions which enable solvation of hydrophobic substrates and products, but do not interfere with stability and yield of the enzymatic reaction.

SUMMARY OF THE INVENTION

The present invention is based on the findings that the performance of chemical synthesis reactions using enzymes as catalyzers can be increased by adding specific surfactants to the reaction mixture. Surfactants may be used in enzymatic synthesis reactions to increase solvation of the reactants and products of the reaction. However, these surfactants negatively affect activity and stability of the enzymes. The present inventors now found that the use of vitamin E derived surfactants such as TPGS-750-M greatly enhances the performance of the enzymatic reaction compared to conventional surfactants or co-solvents. The yield of the reaction is increased, also at lower temperatures, and the reaction is still working even at unfavorable conditions such as low pH values.

In a first aspect, the present invention provides an aqueous reaction mixture comprising an enzyme, a substrate of the enzyme and a surfactant, wherein the surfactant is selected from the group consisting of (i) surfactants having the following formula I:

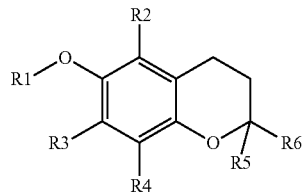

(ii) surfactants having the following formula II:

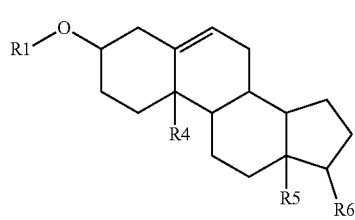

and (iii) surfactants having the following formula III:

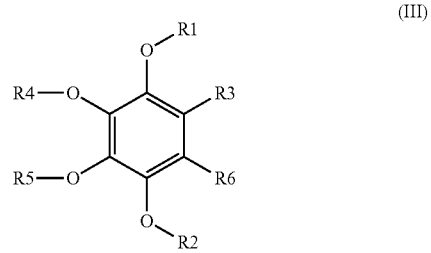

wherein

R1 comprises a poly($C_{1-4}$-alkylene glycol) group;

R2, R3, R4 and R5 are independently hydrogen or $C_{1-4}$-alkyl; and

R6 is $C_{5-80}$-alkyl or $C_{5-80}$-alkenyl.

In a second aspect, the present invention provides a method of performing an enzymatic reaction, comprising the steps of (a) providing a reaction mixture according to the first aspect of the invention, and (b) allowing the enzymatic reaction to proceed.

In a third aspect, the present invention provides the use of a surfactant for increasing the yield and/or the stability of an enzymatic reaction, comprising adding the surfactant to an aqueous mixture comprising an enzyme and a substrate of the enzyme, wherein the surfactant is selected from the group consisting of (i) surfactants having the following formula I:

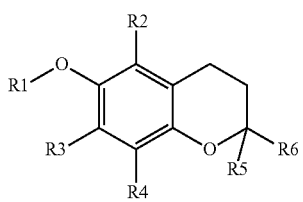
(I)

(ii) surfactants having the following formula II:

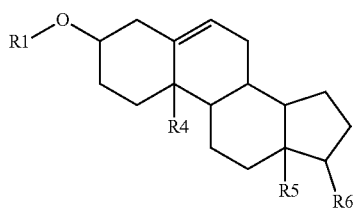
(II)

and
(iii) surfactants having the following formula III:

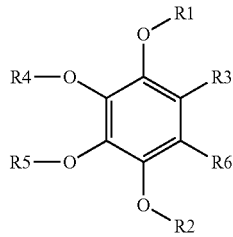
(III)

wherein
R1 comprises a poly($C_{1-4}$-alkylene glycol) group;
R2, R3, R4 and R5 are independently hydrogen or $C_{1-4}$-alkyl; and
R6 is $C_{5-80}$-alkyl or $C_{5-80}$-alkenyl.

The above aspects can be combined. Other objects, features, advantages and aspects of the present invention will become apparent to those skilled in the art from the following description and appended claims. It should be understood, however, that the following description, appended claims, and specific examples, which indicate preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

The present invention provides, in a first aspect, an reaction mixture comprising an enzyme, a substrate of the enzyme and a surfactant, wherein the surfactant is selected from the group consisting of (i) surfactants having the following formula I:

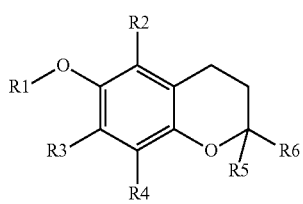
(I)

(ii) surfactants having the following formula II:

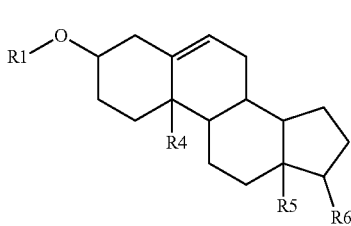
(II)

and
(iii) surfactants having the following formula III:

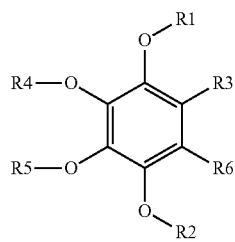
(III)

wherein
R1 comprises a poly($C_{1-4}$-alkylene glycol) group;
R2, R3, R4 and R5 are independently hydrogen or $C_{1-4}$-alkyl; and
R6 is $C_{5-80}$-alkyl or $C_{5-80}$-alkenyl.

The inventive technology is suitable for all chemical reactions which use an enzyme for catalyzing the reaction. It can in particular be used for the synthesis of organic compounds using enzymatic reactions. Suitable enzymes for use in the present reaction mixture include, for example, oxidoreductases, transferases, hydrolases, lyases (synthases), isomerases and ligases (synthetases). Oxidoreductases may catalyze the reduction of C═O and C═C bonds, the reductive amination of C═O groups, and the oxidation of C—H, C═C, C—N, and C—O bonds. Transferases are capable of transferring functional groups such as amino, acyl, phosphoryl, methyl, glycosyl, nitro, and sulfur-containing groups from one compound to another. Hydrolases can catalyze the hydrolysis of esters, amides, lactones, lactams, epoxides, nitriles, and other groups, as well as the respective reverse reactions to form such functionalities. Lyases, also called synthases, may catalyze the addition of small molecules to double bonds such as C═C, C═N, and C═O. Isomerases may catalyze the transformation of isomers (isomerization), including racemizations, epimerizations, and rearrangement reactions. Ligases, also called synthetases, may form complex compounds (in analogy to lyases), using ATP as energy source. In specific embodiments, the enzyme is selected from the group consisting of ketoreductases, ene reductases, transaminases, dehydrogenases such as alcohol dehydrogenases and amino acid dehydrogenases, lipases, esterases and phenylalanine ammonia lyases. Specific examples of the enzyme include ketoreductase, ene reductase and alanine transaminase.

The enzyme is present in the reaction mixture in a concentration suitable to perform the reaction, for example in an amount of about 0.01% to about 100% relative to the amount of the substrate. In particular, the enzyme may be present in an amount of about 0.1% to about 75%, about 0.5% to about 50%, about 1% to about 40%, about 2% to about 30%, about 4% to about 25% or about 5% to about 20% relative to the amount of the substrate. "Amount" in this respect refers either to the weight of the compounds or to the molar amount of the compounds.

In specific embodiments, the aqueous reaction mixture further comprises a co-factor and/or a co-enzyme. The presence and type of the co-factor/co-enzyme depends on the enzymatic reaction which is to be performed. Exemplary co-factors include nicotinamide adenine dinucleotide (NAD), nicotinamide adenine dinucleotide phosphate (NADP), flavin adenine dinucleotide (FAD), and pyridoxal monophosphate. These co-factors may be used to provide protons, electrons and/or amine groups for the enzymatic reaction. NAD, NADP and FAD may be present in the aqueous reaction mixture as ion (e.g. $NAD^+$, $NADP^+$) or protonated (e.g. NADH, NADPH).

The co-factor may be present in the aqueous reaction mixture in stoichiometric amounts. In particular, the molar amount of the co-factor may be at least as high as the molar amount of the substrate. In other embodiments, the amount of the co-factor is lower than the amount of the substrate, in particular in the range of from about 0.01% to about 20%, about 0.05% to about 15%, about 0.1% to about 10%, about 0.25% to about 7.5%, or about 0.5% to about 5% relative to the amount of the substrate. "Amount" in this respect refers either to the weight of the compounds or to the molar amount of the compounds. In these embodiments, preferably the co-factor is regenerated during the reaction, if necessary. For example, the reaction mixture may comprise a further enzyme, optionally with its respective substrate, which regenerates the co-factor. For example, if NAD, NADP or FAD is used as co-factor, the aqueous reaction mixture may further comprise a dehydrogenase such as an alcohol dehydrogenases or a glucose dehydrogenase, and a respective substrate such as an alcohol or glucose.

In other embodiments, the co-factor may be regenerated by the enzyme which also catalyzes the reaction of interest. In these embodiments, a second substrate of this enzyme may be present in the aqueous reaction mixture, in particular in a significantly higher amount than the substrate of interest, such as in an at least 2-fold, preferably at least 4-fold, at least 10-fold, or at least 50-fold molar excess with respect to the substrate of interest. For example, for a transaminase reaction the aqueous reaction mixture may comprise an amine compound such as isopropylamine for regenerating the co-factor such as pyridoxal monophosphate.

In a specific embodiment, the enzyme is a ketoreductase, the substrate is a ketone and the co-factor is NADP. In another embodiment, the enzyme is an ene reductase, the substrate is a compound comprising a carbon-carbon double bond and the co-factor is NAD. In another embodiment, the enzyme is a transaminase, the substrate is a ketone and the co-factor is pyridoxal monophosphate The surfactant in the aqueous reaction mixture is selected from the group consisting of
(i) surfactants having the following formula I:

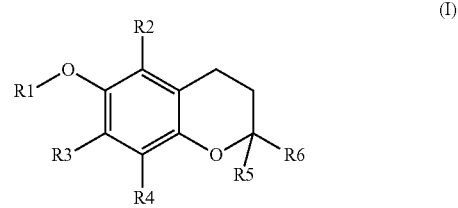

(ii) surfactants having the following formula II:

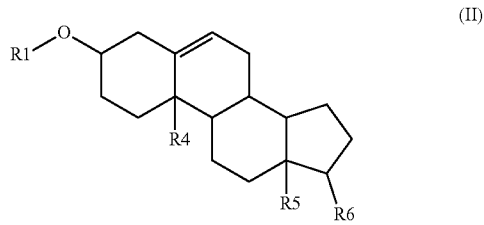

and
(iii) surfactants having the following formula III:

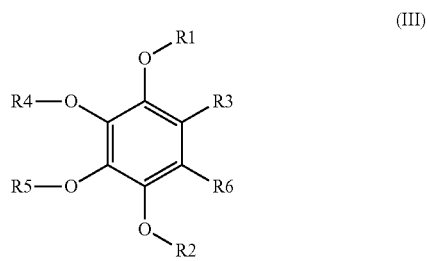

wherein
R1 comprises a poly($C_{1-4}$-alkylene glycol) group;
R2, R3, R4 and R5 are independently hydrogen or $C_{1-4}$-alkyl; and
R6 is $C_{5-80}$-alkyl or $C_{5-80}$-alkenyl.

The surfactant in the aqueous reaction mixture can be any surfactant according to formula (I), formula (II) or formula (III). In certain embodiments, the surfactant has a molecular weight of 10,000 g/mol or less, in particular 7,500 g/mol or less, 5,000 g/mol or less, 3,000 g/mol or less, 2,500 g/mol or less or even 2,000 g/mol or less.

In particular, the surfactant should not interfere with the chemical reaction. In certain embodiments, the surfactant is a non-ionic surfactant. The surfactant generally is amphiphilic and comprises a hydrophilic part and a hydrophobic part. The hydrophilic part is mainly formed by the residue R1 and the hydrophobic part is mainly formed by the residue R6. In specific embodiments, the surfactant is able to form micelles in the surfactant-water mixture.

The surfactant comprises a poly($C_{1-4}$-alkylene glycol) group in residue R1. This poly($C_{1-4}$-alkylene glycol) group especially is a poly(ethylene glycol) group or a poly(propylene glycol) group, in particular a poly(ethylene glycol) group. The poly($C_{1-4}$-alkylene glycol) group may also consist of a mixture of different poly($C_{1-4}$-alkylene glycol) groups, such as a mixture of poly(ethylene glycol) and poly(propylene glycol). R1 in particular comprises a poly ($C_{2-3}$-alkylene glycol) group. The poly($C_{1-4}$-alkylene glycol) group, especially the poly(ethylene glycol) group, may have an average molecular weight in the range of about 100 to about 10,000 g/mol, especially in the range of about 200 to about 5,000 g/mol, in particular in the range of about 250 to 2500 g/mol, about 400 to about 2,000 g/mol or about 500 to 1500 g/mol, such as about 550, about 750 or about 1000 g/mol.

The poly($C_{1-4}$-alkylene glycol) group of residue R1 may be attached to the oxygen atom of the core structure via a covalent bond or a linking group. The linking group may be any chemical linker suitable for attaching the poly($C_{1-4}$-alkylene glycol) group to the oxygen atom. In particular, the linking group may be a dicarboxylic acid which forms ester linkages to the core structure and the poly($C_{1-4}$-alkylene glycol) group. Exemplary linking groups include dicarboxylic acid having 2 to 20 carbon atoms, such as succinic acid, sebacic acid, malonic acid, glutaric acid, adipic acid, maleic acid and fumaric acid.

In certain embodiments, R1 further comprises a terminal group attached to the end of the poly($C_{1-4}$-alkylene glycol) group. This terminal group in particular is attached to the poly($C_{1-4}$-alkylene glycol) group via an ether, ester or amide linkage. The terminal group especially is a $C_{1-18}$ alkyl or alkenyl group, in particular a $C_{1-8}$ alkyl group such as a $C_{1-4}$ alkyl group. In certain embodiments, the terminal group is a methyl group attached to the poly($C_{1-4}$-alkylene glycol) group via an ether linkage.

In specific embodiments, R1 consists of the poly($C_{1-4}$-alkylene glycol) group, the linking group and the terminal group as described herein.

R2, R3, R4 and R5 are independently hydrogen or $C_{1-4}$-alkyl, in particular hydrogen, methyl or ethyl, especially hydrogen or methyl. In certain embodiments, R5 is methyl. In certain embodiments, R4 is methyl. In certain embodiments, R4 and R5 are methyl. In Further embodiments, R2 and R3 are independently hydrogen or methyl. In specific embodiments, R4 and R5 are methyl and R2 and R3 are independently hydrogen or methyl. In certain embodiments where the surfactant has formula (I), R2, R3, R4 and R5 are all methyl. In certain embodiments where the surfactant has formula (II), R4 and R5 are all methyl. In certain embodiments where the surfactant has formula (III), R2 is hydrogen and R3, R4 and R5 are methyl.

R6 is $C_{5-80}$-alkyl or $C_{5-80}$-alkenyl. R6 may be linear or branched and may contain cyclic groups including aromatic groups. In certain embodiments, R6 does not contain cyclic groups or aromatic groups. In particular, R6 is branched.

In embodiments where the surfactant has formula (I), R6 may be $C_{5-30}$-alkyl or $C_{5-30}$ alkenyl, especially $C_{8-25}$-alkyl or $C_{8-25}$-alkenyl, in particular $C_{10-20}$-alkyl or $C_{10-20}$-alkenyl, preferably $C_{14-18}$-alkyl or $C_{14-18}$-alkenyl. The alkenyl group may comprise one or more carbon-carbon double bonds, in particular one, two, three, four or five double bonds, such as two or three, especially three. In specific embodiments, R6 is $C_{16}$-alkyl or $C_{16}$-alkenyl, in particular 4,8,12-trimethyltridecyl or 4,8,12-trimethyl-3,7,11-tridecatrienyl. In certain embodiments, the carbon atom carrying R5 and R6 is in R conformation.

In embodiments where the surfactant has formula (II), R6 may be $C_{5-20}$-alkyl or $C_{5-20}$ alkenyl, especially $C_{6-18}$-alkyl or $C_{6-18}$-alkenyl, in particular $C_{7-15}$-alkyl or $C_{7-15}$-alkenyl, preferably $C_{8-12}$-alkyl or $C_{8-12}$-alkenyl. In specific embodiments, R6 is $C_{10}$-alkyl, in particular 5-ethyl-6-methylheptan-2-yl.

In embodiments where the surfactant has formula (III), R6 may be $C_{30-80}$-alkyl or $C_{30-80}$-alkenyl, especially $C_{35-70}$-alkyl or $C_{35-70}$-alkenyl, in particular $C_{40-60}$-alkyl or $C_{40-60}$-alkenyl, preferably $C_{45-55}$-alkyl or $C_{45-55}$-alkenyl. The alkenyl group may comprise one or more carbon-carbon double bonds, in particular five, eight or ten double bonds, especially ten. In specific embodiments, R6 is $C_{50}$-alkenyl, in particular 3,7,11,15,19,23,27,31,35,39-decamethyltetraconta-2,6,10,14,18,22,26,30,34,38-decanyl.

In embodiments where the surfactant has formula (I), the surfactant especially is derived from vitamin E, in particular from tocopherol, especially from α-tocopherol. Certain examples of the surfactant include tocopherol polyethylene glycol succinates (TPGS), in particular DL-α-tocopherol polyethylene glycol succinates such as TPGS-750-M, TPGS-1000, TPGS-1500, TPGS-400, TPGS-1100-M, TPGS-2000, TPGS-860-oleate, TPGS-PEG-PPG-PEG-1100 and TPGS-PPG-PEG-70-butyl, and DL-α-tocopherol polypropylene glycol succinates such as TPPG-1000 and TPPG-1000-butyl; and polyethylene glycol α-tocopherol diester of sebacic acid (PTS) such as PTS-600. In specific embodiments, the surfactant is selected from the group consisting of TPGS-750-M, TPGS-1000 and PTS, in particular TPGS-750-M.

In embodiments where the surfactant has formula (II), the surfactant especially is derived from ubiquinol. Certain examples of the surfactant include polyethyleneglycol ubiquinol succinate (PQS), in particular PQS comprising mPEG such as mPEG2000.

In embodiments where the surfactant has formula (III), the surfactant especially is derived from sitosterol, in particular β-sitosterol. Certain examples of the surfactant include β-sitosterol methoxyethyleneglycol succinate (Nok), in particular Nok comprising mPEG such as mPEG550.

The concentration of the surfactant in the aqueous reaction mixture in particular is at least 0.01% (w/w), in particular at least 0.02% (w/w), especially at least 0.5% (w/w) or at least 1% (w/w). In specific embodiments, the concentration of the surfactant in the aqueous reaction mixture is in the range of 0.01 to 20% (w/w), in particular in the range of 0.02 to 15% (w/w), in the range of 0.1 to 10% (w/w), 0.2 to 7.5% (w/w) or 0.5 to 5% (w/w), especially in the range of 0.75 to 3% (w/w), such as about 1% (w/w), about 1.5% (w/w) or about 2% (w/w). In specific embodiments, the concentration of the surfactant in the surfactant-water mixture is above its critical micellar concentration.

In certain embodiments, the aqueous reaction mixture further comprises a buffer. The buffer in particular should be suitable to keep the pH of the reaction mixture at or about a neutral pH. In particular, the buffer is selected from the group consisting of TRIS, phosphate, citrate, acetate and ammonia. The aqueous reaction mixture preferably has a pH at which the enzyme is active and stable and/or which is suitable for the enzymatic reaction. In certain embodiments, the pH value is in the range of from 4.0 to 10.0, in particular from 6.0 to 8.0, especially from 6.5 to 7.5, such as about 7.0.

The substrate in the reaction mixture may be any substrate suitable for performing the enzymatic reaction. The substrate in particular depends on the type of enzymatic reaction which is to be performed in the reaction mixture. The reaction mixture may also comprise more than one substrate, such as two substrates or three substrates. In specific embodiments, the substrate and/or the product of the enzymatic reaction is not water-miscible or only partly water-miscible. A compound which is only partly water-miscible in particular is only miscible with water at a concentration of 20 g/l or less, especially 10 g/l or less or 5 g/l or less, at room temperature. The substrate can be used in any concentration which is feasible for performing the chemical reaction. In particular, the substrate is used at high concentrations. For example, the concentration of the substrate in the reaction mixture is at least 0.1 M, in particular at least 0.5 M, at least 1.0 M, at least 1.1 M, at least 1.2 M, at least 1.3 M, at least 1.5 M, at least 1.7 M or at least 2.0 M. The person skilled in the art is able to select suitable substrates and their concentrations.

In certain embodiments, the aqueous reaction mixture may additionally comprise a co-solvent. The co-solvent may in particular be an organic solvent or a further surfactant or a mixture of these.

The organic solvent may be any organic solvent. Preferably, it shall not disturb or inhibit the enzymatic reaction. In certain embodiments, the organic solvent is water-miscible or partly water-miscible. The organic solvent especially is an aprotic organic solvent. Suitable examples of the organic solvent include acetone, tetrahydrofuran (THF) and derivatives thereof such as methyl tetrahydrofuran, pyridine, polyethylene glycol (PEG), polypropylene glycol (PPG), in particular PEG with an average molecular weight of about 100 g/mol to about 2000 g/mol such as PEG200, PEG600, PEG1000 and PEG2000, derivatives thereof such as mono- or dialkyl PEG, in particular mono- or dimethyl PEG, mono- or diethyl PEG and mono- or dipropyl PEG. Further examples include acetonitrile, dimethylformamide (DMF), dichloromethane (DCM), toluene, and alcohols such as a $C_{1-10}$ aliphatic alcohol, in particular 2-butyl alcohol. In certain embodiments, the amount of the organic solvent in the reaction mixture is in the range of from 0.1% to 50% (v/v), in particular from 1% to 40% (v/v), from 2% to 30% (v/v), from 4% to 25% (v/v) or from 5% to 20% (v/v).

The further surfactant may be any surfactant. Preferably, it shall not disturb or inhibit the enzymatic reaction. In certain embodiments, the hydrophilic part of the surfactant comprises a polyalkylene glycol moiety, especially a polyethylene glycol moiety or a polypropylene glycol moiety. The polyalkylene moiety, especially the polyethylene glycol moiety, may have an average molecular weight in the range of about 100 to about 10,000 g/mol, especially in the range of about 300 to about 3,000 g/mol, in particular in the range of about 400 to about 2,000 g/mol. Certain examples of the further surfactant comprising a polyalkylene glycol moiety include Triton X-100; polyethylene glycol alkyl ethers such as Brij surfactants, in particular Brij 30, Brij 35, Brij 52, Brij 56, Brij 58, Brij 72, Brij 76, Brij 78, Brij 92, Brij 96, Brij 98, Cremophor A6, Cremophor A25 and Thesit; polyethylene glycol esters such as polyethylene glycol (15)-hydroxystearate (Solutol HS 15); polyethylene glycol sorbitan fatty acid esters, also known as polysorbates or Tween, such as polysorbate 20, polysorbate 21, polysorbate 40, polysorbate 60, polysorbate 61, polysorbate 65, polysorbate 80, polysorbate 81, polysorbate 85 and polysorbate 120; cholesteryl PEG succinates such as cholesteryl PEG1000 succinate; (deoxy) cholic PEG such as colic PEG1000 and deoxy-cholic PEG1000; chromanol polyethylene glycol succinates such as Chrom-400 and Chrom-1000; and other derivatives of PEG such as $C_4$-azo-PEG; cetyltrimethylammonium bromide (CTAB); phase transfer surfactants such as sodium deoxycholate; and octanoic acid and other long alkyl chain acids, in particular $C_{6-20}$ alkyl chain acids. The concentration of the further surfactant in the aqueous reaction mixture in particular may be in the range of 0.1 to 10% (w/w). In certain embodiments, the concentration of the further surfactant is in the range of 0.5 to 5% (w/w), especially in the range of 0.8 to 4% (w/w), 1 to 3% (w/w) or 1.5 to 2.5% (w/w), such as about 2% (w/w).

The present technology is especially useful for applications where high substrate concentrations in the reaction mixture are desire, such as at very large scales or very small scales. In one embodiment, the reaction mixture is of industrial scale. It may for example have a volume of at least 1 l, in particular at least 10 l, at least 100 l, or at least 1000 l. In another embodiment, the reaction mixture is of microscale. It may for example have a volume of 10 ml or less, in particular 1 ml or less, 100 µl or less, 10 µl or less or 1 µl or less.

The reaction mixture is a charge or batch mixture for performing a chemical reaction. In certain embodiments the reaction mixture does not comprise any products of the enzymatic reaction or comprises only residual amount of any products of the enzymatic reaction. In other embodiments, it may also contain a significant amount of the product of the enzymatic reaction.

In a second aspect, the present invention provides a method of performing an enzymatic reaction, comprising the steps of (a) providing an aqueous reaction mixture as described herein, and (b) allowing the enzymatic reaction to proceed.

The reaction mixture especially comprises an enzyme, a substrate of the enzyme and a surfactant, wherein the surfactant is selected from the group consisting of (i) surfactants having the following formula I:

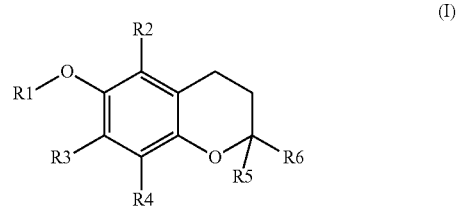

(ii) surfactants having the following formula II:

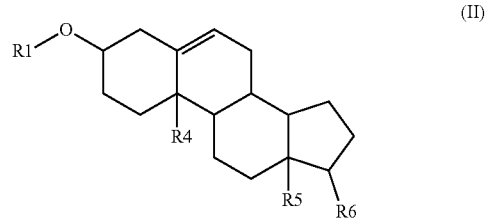

and
(iii) surfactants having the following formula III:

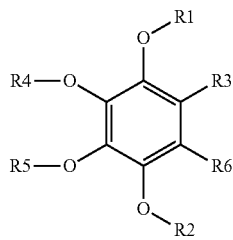

wherein
R1 comprises a poly($C_{1-4}$-alkylene glycol) group;
R2, R3, R4 and R5 are independently hydrogen or $C_{1-4}$-alkyl; and
R6 is $C_{5-4}$-alkyl or $C_{1-4}$-alkenyl.

The aqueous reaction mixture in particular may exhibit any of the features, embodiments and examples described herein including combinations thereof.

The enzymatic reaction may be any chemical reactions which can be performed using an enzyme for catalyzing the reaction. In particular organic chemical synthesis reactions can be performed, for example with at least partly hydrophobic compounds. Exemplary chemical reactions include reduction reactions, oxidation reactions, amination reactions, nitrilation reactions, hydrolysis reactions, esterification reactions and amidation reactions such as acylations. The enzyme and substrate in the aqueous reaction mixture are suitable for the specific chemical reaction. In particular, the enzyme and substrate are specifically chosen so that the enzymatic reaction proceeds as desired. Suitable enzymes and substrates are described herein.

In certain embodiments, the enzymatic reaction is allowed to proceed in step (b) at reaction conditions suitable for performing the enzymatic reaction. In particular, the reaction conditions include a temperature of 80° C. or less, especially 60° C. or less, 45° C. or less, or 40° C. or less. In particular, the enzymatic reaction is performed at a temperature in the range of 10° C. to 50° C., in particular 20° C. to 45° C. or 25° C. to 40° C. For example, the enzymatic reaction may be allowed to proceed at about 37° C., at about 30° C. or at about room temperature. In specific embodiments, the reaction mixture is agitated, in particular stirred, during the course of the enzymatic reaction.

Furthermore, the reaction conditions in particular include a pH value in the range of 4.0 to 10.0, in particular 5.0 to 9.5, 5.5 to 9.0, 6.0 to 8.5 or 6.5 to 8.0. In certain embodiments, the pH is held constant during the enzymatic reaction, in particular within a range of +/−1.0 pH units, especially within +/−0.5 pH units around the pH desired value. In other embodiments, however, the pH value is allowed to vary by more than 1.0 pH units, in particular by more than 1.5 pH units or even more than 2.0 pH units. The aqueous reaction mixture as described herein is able to stabilize the enzyme so that a variation in pH does not significantly affect the enzymatic reaction.

The methods of performing an enzymatic reaction may comprise the further step of isolating the product of the enzymatic reaction. In particular, this step is performed after completion of the enzymatic reaction. The product is in particular separated from one or more, in particular essentially all of the other components of the aqueous reaction mixture. For example, the product is separated from the remaining substrate, side products, the enzyme, the surfactant, co-enzymes, co-factors and/or organic solvents. Isolation of the product may be achieved by means and techniques known in the art, including for example evaporation of solvents, aggregation or crystallization and filtration, phase separation, chromatographic separation and others.

The present invention improves the solubility of the substrates and products in the aqueous reaction mixture and enhances stability of the enzyme. Thereby, the yield of the enzymatic reaction is increased and the amount of unwanted side products obtained by the enzymatic reaction is reduced. In view of this, the present invention in a further aspect provides the use of a surfactant for increasing the yield of an enzymatic reaction, comprising adding the surfactant to an aqueous mixture comprising an enzyme and a substrate of the enzyme, wherein the surfactant is selected from the group consisting of
(i) surfactants having the following formula I:

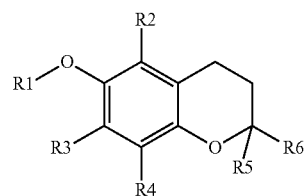

(ii) surfactants having the following formula II:

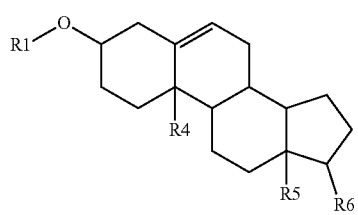

and
(iii) surfactants having the following formula III:

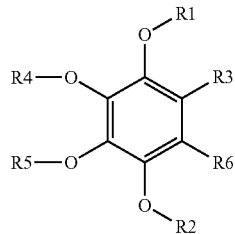

wherein
R1 comprises a poly($C_{1-4}$-alkylene glycol) group;
R2, R3, R4 and R5 are independently hydrogen or $C_{1-4}$-alkyl; and
R6 is $C_{5-80}$-alkyl or $C_{5-80}$-alkenyl.

In a further aspect, the present invention provides the use of a surfactant for increasing the stability of an enzymatic reaction, comprising adding the surfactant to an aqueous mixture comprising an enzyme and a substrate of the enzyme, wherein the surfactant is selected from the group consisting of (i) surfactants having the following formula I:

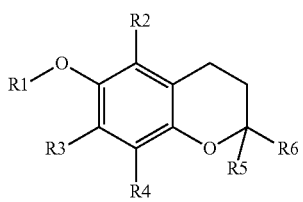

(ii) surfactants having the following formula II:

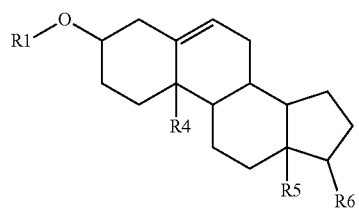

and
(iii) surfactants having the following formula III:

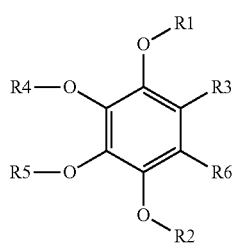

wherein
R1 comprises a poly($C_{1-4}$-alkylene glycol) group;
R2, R3, R4 and R5 are independently hydrogen or $C_{1-4}$-alkyl; and
R6 is $C_{5-80}$-alkyl or $C_{5-80}$-alkenyl.

An increased stability of the enzymatic reaction in particular includes an increased stability of the enzyme in the reaction mixture.

The embodiments, features and examples described herein, including combinations thereof, for methods of performing an enzymatic reaction and aqueous reaction mixtures likewise apply to the use of a surfactant for increasing the yield and/or the stability of an enzymatic reaction.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements may and/or indeed does encompass further elements as well as embodiments wherein the subject-matter which "comprises" specifically listed elements does not comprise further elements. Likewise, the expression "have" is to be understood as the expression "comprise", also including and specifically referring to the expressions "consist essentially of" and "consist of".

Numeric ranges described herein are inclusive of the numbers defining the range. The headings provided herein are not limitations of the various aspects or embodiments of this invention which can be read by reference to the specification as a whole. According to one embodiment, subject matter described herein as comprising certain steps in the case of methods or as comprising certain ingredients in the case of compositions refers to subject matter consisting of the respective steps or ingredients.

It is preferred to select and combine specific aspects and embodiments described herein and the specific subject-matter arising from a respective combination of specific embodiments also belongs to the present disclosure.

FIGURE LEGEND

FIG. 1 shows a comparison of the reaction kinetics in different reaction media. Reaction conditions: In each vial was added 20 mg of ketone 1, 5 mg of KRED-EW124, 5 mg GDH, 2 mg NADP, 25 mg glucose, 2 mM $MgCl_2$ in the cosolvent systems as listed. pH=7, temperature=30° C. HPLC analyses of the reaction mixture were carried out at the specified time.

EXAMPLES

Example 1: Synthesis of Benzyl (R)-4-hydroxy-2-(4-(methoxycarbonyl)phenyl)piperidine-1-carboxylate Using Ketoreductase Surfactants have been applied in biocatalysis in modulating enzyme activities with beneficial effects, such as increasing the solubility of reactants and enhancing reaction selectivity. Although a number of surfactants including ionic liquids, SDS and Triton X have been utilized in a wide range of biotransformations, TPGS-750-M as an alternative surfactant developed in the Lipshutz lab has not been investigated in biocatalysis. During the investigations of a ketoreductase (KRED) mediated reaction as shown in scheme 1, the low solubility of both starting ketone 1 and product alcohol 2 necessitated significant efforts to search for a suitable reaction media for this heterogeneous reaction.

Scheme 1

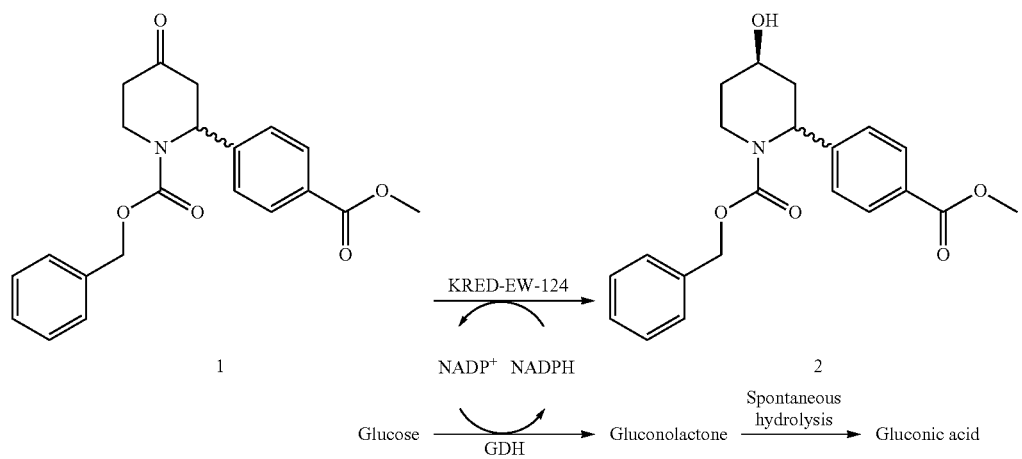

First, a number of co-solvent systems including TPGS, PEG400 and DMSO in aqueous solutions were employed under parallel screening conditions for the above reaction. As shown in FIG. 1, during the first phase of the reaction within 2.5 h, TPGS performed better than PEG400 and DMSO with a 10% conversion difference. As the reaction proceeded further, the reaction is significantly faster in TPGS and a conversion difference of around 40% was observed as compared to the reaction in PEG400 and DMSO within 6 h. After 22 h, the reaction came to essentially complete conversion in TPGS (100%) while the reaction in PEG400 and DMSO stopped at 82% and 86% conversions, respectively. This phenomenon reflected the less stability of the ketoreductase in the organic solvent additives of both PEG400 and DMSO system.

With the screening results in hand, we further optimized the reaction in gram scale. Especially we compared the performance of TPGS and DMSO system. Thus the reactions were carried out in 2% TPGS and 15% DMSO aqueous solution respectively at 40° C. using a 5 w % of enzyme loading. The reaction reached 93% conversion after 18 h in TPGS system while a lower 80% conversion after 20 h in DMSO system. More importantly, the reaction continued and reached 98.8% conversion in TPGS after additional 25 h. But an additional 2 wt % enzyme has to be added to push the reaction to 98.6% conversion in DMSO (entry 1, table 1). This observation clearly demonstrated the more active and stable nature of the enzyme in TPGS as compared to DMSO. Another interesting observation was that after an accidental exposure of the enzyme under pH 4.7 for 24 h in the reaction system of TPGS and readjustment of pH to 7, the enzyme is still active enough to catalyze the reaction further with the same activity (entry 2, table 1). The superior stability could be afforded by the molecular interactions between the TPGS and protein and the catalytic active site of the enzyme is protected from the aqueous reaction media.

TABLE 1

Comparison of ketoreductase in TPGS and DMSO

| Conditions | 2% TPGS-750M | DMSO/water |
|---|---|---|
| Conversion @ 40° C. (with 5% enzyme) | 93% for 18 h; up to 98.8% for additional 25 h without additional enzymes | 80% for 20 h; up to 98.6% for additional 32 h, but 2% more enzyme necessary |
| Enzyme activity | Still active for 6 d, even pH drop to 4.7 for 24 h @ rt | pH should be constant 6.9-7.1 for active catalysis |

Finally the reaction in TPGS is more amenable to scale up, and compound 1 can be added in solid form without preformation of a solution or milling to reduce the particle size. A typical experimental procedure is as follows: to a degassed 2% weight solution of TPGS-750-M in buffer water (34 mL, 10 v; stock solution prepared from 74 mL of 2 wt % TPGS-750-M water solution, 1.6 g of Na$_2$HPO$_4$.12H$_2$O and 0.5 g of NaH$_2$PO$_4$.2H$_2$O) was added glucose (3.2 g, 18 mmol, 2.0 eq) in a mechanically stirred reactor equipped with pH/ORP controller at rt. The suspension was stirred at rt for 20 minutes, and to the resulting mixture was sequentially added NADP (59 mg, 68% purity), GDH (33 mg) and ketoreductase (0.16 g, 5 wt % of substrate 1). Then substrate 1 (3.3 g, 9 mmol, 1.0 eq) was added and the pH of the reaction mixture was adjusted to 6.8-7.2 by addition of 1M aqueous NaOH at rt. The resulting reaction mixture was heated to 40° C. and stirred at 40° C. for 43 hr until completion of the reaction as determined by HPLC. As the reaction proceeded, the product 2 precipitated out from the reaction mixture and formed a suspension. The resulting suspension was filtered at 40° C., and the resulting wet cake was washed with water and dried to give product 2 as an off-white solid (2.8 g, purity 97%, yield 85%).

Scheme 2

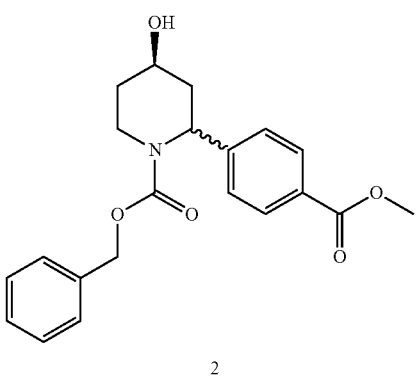

In conclusion, a beneficial effect of TPGS as an additive in a ketoreductase mediated biotransformation was shown, including superior reaction kinetics and process robustness. The underlying enzyme stability in TPGS will find similar benefits when applied to a wide range of biocatalytic transformations.

Example 2: Synthesis of (R)-5-fluoro-3-(3-fluorophenyl)-2-(1-hydroxyethyl-4H-chromen-4-one Using Ketoreductase Reaction Mixture:
20 mg substrate 3
enzyme ketoreductase KRED-EW-109 (amount: see table 2)
20 mg D-glucose
0.4 mg (2% (m/m)) glucose dehydrogenase (GDH)
0.2 mg (1% (m/m)) NADP
0.1M PBS (amount: see table 2)
2% TPGS-750-M (m/m) in 0.1M PBS (amount: see table 2)
DMSO (amount: see table 2)
Reaction Conditions: pH 7.0, 30° C.

TABLE 2

| No. | enzyme | 0.1M PBS | 2% TPGS in PBS | DMSO (v/v) | Conversion 17.5 h | 24 h |
|---|---|---|---|---|---|---|
| 1 | 1 mg 5.0% (m/m) | 0.9 ml | N.A. | 0.1 ml 10% (v/v) | 72.6% | 67.5% |
| 2 | N.A. | 1 ml | N.A. | 87.2% | 87.2% |
| 3 | 0.2 mg 1.0% (m/m) | 0.9 ml | N.A. | 0.1 ml 10% (v/v) | 3.9% | 4.1% |
| 4 | N.A. | 1 ml | N.A. | 11.7% | 13.2% |
| 5 | 0.1 mg 0.5% (m/m) | 0.9 ml | N.A. | 0.1 ml 10% (v/v) | 1.5% | 1.5% |
| 6 | N.A. | 1 ml | N.A. | 7.9% | 9.3% |
| 7 | 1 mg 5.0% (m/m) | 0.9 ml | N.A. | 0.1 ml 10% (v/v) | 63.2% | 61.0% |
| 8 | 0.5 ml | 0.5 ml | N.A. | 89.9% | 90.4% |
| 9 | 0.2 mg 1.0% (m/m) | 0.9 ml | N.A. | 0.1 ml 10% (v/v) | 2.1% | 2.5% |
| 10 | 0.5 ml | 0.5 ml | N.A. | 12.6% | 14.4% |
| 11 | 0.1 mg 0.5% (m/m) | 0.9 ml | N.A. | 0.1 ml 10% (v/v) | 1.2% | 1.6% |
| 12 | 0.5 ml | 0.5 ml | N.A. | 7.6% | 8.4% |

Scheme 3

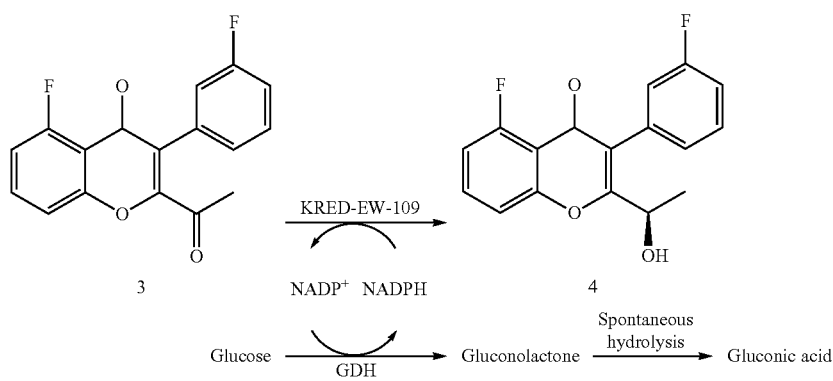

Example 3: Synthesis of 1-phenylethanol Using Ketoreductase

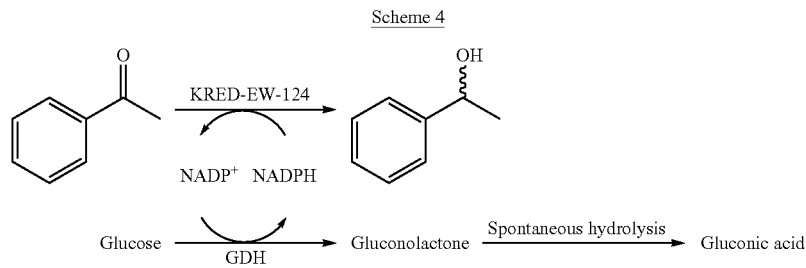

Scheme 4

Reaction Mixture:
20 μl acetophenone
enzyme ketoreductase KRED-EW-124 (amount: see table 3)
20 mg D-glucose
0.4 mg (2% (m/m)) glucose dehydrogenase (GDH)
0.2 mg (1% (m/m)) NADP
0.1M PBS (amount: see table 3)
2% TPGS-750-M (m/m) in 0.1M PBS (amount: see table 3)
DMSO (amount: see table 3)
Reaction Conditions: pH 7.0, 30° C.

TABLE 3

| No. | enzyme | 0.1M PBS | 2% TPGS in PBS | DMSO (v/v) | Conversion 18 h |
|---|---|---|---|---|---|
| 1 | 8 mg 40% (m/m) | 0.9 ml | N.A. | 0.1 ml 10%(v/v) | 53.5% |
| 2 | N.A. | N.A. | 1 ml | N.A. | 55.0% |
| 3 | 4 mg 20% (m/m) | 0.9 ml | N.A. | 0.1 ml 10%(v/v) | 48.7% |
| 4 | N.A. | N.A. | 1 ml | N.A. | 52.4% |
| 5 | 2 mg 10% (m/m) | 0.9 ml | N.A. | 0.1 ml 10%(v/v) | 45.2% |
| 6 | N.A. | N.A. | 1 ml | N.A. | 47.5% |
| 7 | 8 mg 40% (m/m) | 0.9 ml | N.A. | 0.1 ml 10%(v/v) | 53.2% |
| 8 | | 0.5 ml | 0.5 ml | N.A. | 52.5% |
| 9 | 4 mg 20% (m/m) | 0.9 ml | N.A. | 0.1 ml 10%(v/v) | 47.9% |
| 10 | | 0.5 ml | 0.5 ml | N.A. | 50.6% |
| 11 | 2 mg 10% (m/m) | 0.9 ml | N.A. | 0.1 ml 10%(v/v) | 43.3% |
| 12 | | 0.5 ml | 0.5 ml | N.A. | 45.2% |

Example 4: Synthesis of (S)-3-(3-bromopyridin-4-yl)-methylcyclohexan-1-one Using Ene Reductase

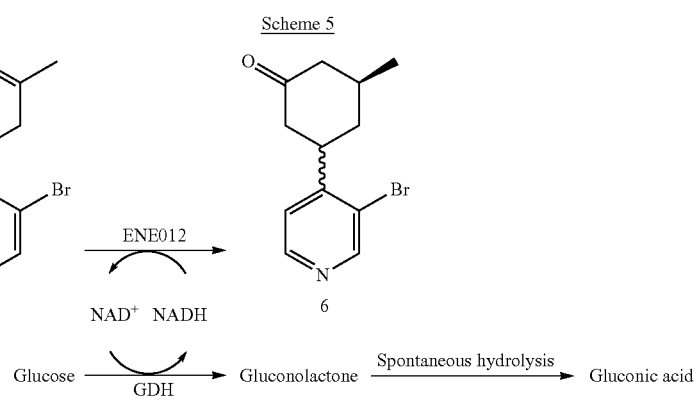

Scheme 5

Reaction Mixture:
20 μl substrate 5
enzyme ene reductase ENE012 (amount: see table 4)
20 mg D-glucose
0.4 mg (2% (m/m)) glucose dehydrogenase (GDH)
0.2 mg (1% (m/m)) NAD
0.1M PBS (amount: see table 4)
2% TPGS-750-M (m/m) in 0.1M PBS (amount: see table 4)
toluene (amount: see table 4)
Reaction Conditions: pH 7.0, 30° C.

TABLE 4

| No. | enzyme | 0.1M PBS | 2% TPGS in PBS | Toluene (v/v) | Conversion 19.5 h | 43.5 h |
|---|---|---|---|---|---|---|
| 1 | 4 mg 20% (m/m) | 0.8 ml | N.A. | 0.2 ml 20% (v/v) | 45.8% | 36.7% |
| 2 |  | N.A. | 1 ml | N.A. | 82.7% | 79.9% |
| 3 | 2 mg 10% (m/m) | 0.8 ml | N.A. | 0.2 ml 20% (v/v) | 30.9% | 33.8% |
| 4 |  | N.A. | 1 ml | N.A. | 42.3% | 69.3% |
| 5 | 4 mg 20% (m/m) | 0.8 ml | N.A. | 0.2 ml 20% (v/v) | 47.8% | 44.4% |
| 6 |  | 0.5 ml | 0.5 ml | N.A. | 62.3% | 59.0% |
| 7 | 2 mg 10% (m/m) | 0.8 ml | N.A. | 0.2 ml 20% (v/v) | 28.1% | 28.2% |
| 8 |  | 0.5 ml | 0.5 ml | N.A. | 47.6% | 75.2% |

The invention claimed is:

1. An aqueous, enzyme-catalyzed chemical synthesis reaction mixture comprising: an enzyme, a substrate of the enzyme and a surfactant, wherein the enzyme is selected from the group consisting of reductases, transferases, dehydrogenases, lipases, and esterases, further wherein the surfactant is present in the reaction mixture above its critical micellar concentration and is selected from the group consisting of:

(i) surfactants having the following formula I:

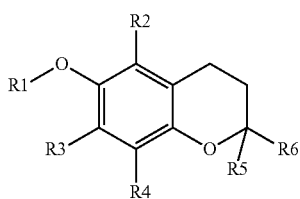

(ii) surfactants having the following formula II:

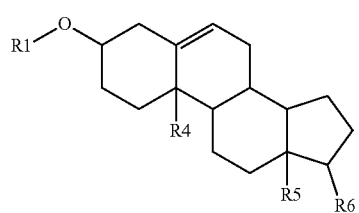

and
(iii) surfactants having the following formula III:

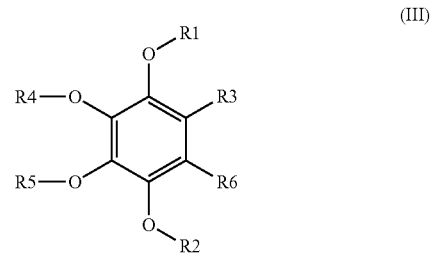

wherein
R1 comprises a poly($C_{1-4}$-alkylene glycol) group;
R2, R3, R4 and R5 are independently hydrogen or $C_{1-4}$-alkyl; and
R6 is $C_{5-80}$-alkyl or $C_{5-80}$-alkenyl.

2. The reaction mixture according to claim 1, wherein R1 is a poly($C_{1-4}$-alkylene glycol) group, which is attached to the oxygen atom of the core structure via a covalent bond or a linking group, and which optionally comprises a terminal $C_{1-4}$-alkyl group.

3. The reaction mixture according to claim 2, wherein the linking group is a dicarboxylic acid which forms ester linkages to the core structure and the poly($C_{1-4}$-alkylene glycol) group.

4. The reaction mixture according to claim 3, wherein the linking group is a dicarboxylic acid having 2 to 20 carbon atoms selected from the group consisting of succinic acid and sebacic acid.

5. The reaction mixture according to claim 2, wherein the terminal $C_{1-4}$-alkyl group is methyl.

6. The reaction mixture according to claim 1, wherein the poly($C_{1-4}$-alkylene glycol) group is a poly(ethylene glycol) group.

7. The reaction mixture according to claim 1, wherein the poly($C_{1-4}$-alkylene glycol) group has an average molecular weight of about 250 to 2500 g/mol.

8. The reaction mixture according to claim 1, wherein R5 is methyl.

9. The reaction mixture according to claim 1, wherein R4 is methyl.

10. The reaction mixture according to claim 1, wherein R2 and R3 are independently hydrogen or methyl.

11. The reaction mixture according to claim 1, wherein
(i) the surfactant has formula (I) and R2, R3, R4 and R5 are all methyl; or
(ii) the surfactant has formula (II) and R4 and R5 are methyl; or
(iii) the surfactant has formula (III) and R2 is hydrogen and R3, R4 and R5 are methyl.

12. The reaction mixture according to claim 1, wherein R6 is branched or linear.

13. The reaction mixture according to claim 1, wherein
(i) the surfactant has formula (I) and R6 is $C_{8-25}$-alkyl or $C_{8-25}$-alkenyl; or
(ii) the surfactant has formula (II) and R6 is $C_{5-20}$-alkyl or $C_{5-20}$-alkenyl or
(iii) the surfactant has formula (III) and R6 is $C_{30-80}$-alkyl or $C_{30-80}$-alkenyl.

14. The reaction mixture according to claim 13, wherein
(i) the surfactant has formula (I) and R6 is $C_{1-6}$-alkyl or $C_{1-6}$-alkenyl; or
(ii) the surfactant has formula (II) and R6 is $C_{10}$-alkyl; or
(iii) the surfactant has formula (III) and R6 is $C_{50}$-alkenyl.

15. The reaction mixture according to claim 1, wherein the surfactant has formula (I) and is a vitamin E-derived compound.

16. The reaction mixture according to claim 15, wherein the surfactant is selected from the group consisting of a D-a-tocopherol poly(ethylene glycol) succinate (TPGS)-750-M (TPGS-750-M), TPGS-1000, and PEG-600/alpha-tocopherol-based diester of sebacic acid (PTS).

17. The reaction mixture according to claim 1, wherein the surfactant has formula (II) and is an ubiquinol-derived compound.

18. The reaction mixture according to claim 17, wherein the surfactant is polyethyleneglycol ubiquinol succinate (PQS).

19. The reaction mixture according to claim 1, wherein the surfactant has formula (II) and is a β-sitosterol-derived compound.

20. The reaction mixture according to claim 19, wherein the surfactant is β-sitosterol methoxyethyleneglycol succinate (Nok).

21. The reaction mixture according to claim 1, wherein the enzyme is selected from the group consisting of ketoreductases, ene reductases, transaminases, alcohol dehydrogenases, and amino acid dehydrogenases.

22. The reaction mixture according to claim 1, further comprising a co-enzyme or a co-factor.

23. The reaction mixture according to claim 22, wherein the co-enzyme or co-factor is selected from the group consisting of alcohol dehydrogenases, NAD, NADP, FAD and pyridoxal monophosphate.

24. The reaction mixture according to claim 22, wherein the enzyme is a ketoreductase, the substrate is a ketone and the co-factor is NADP.

25. The reaction mixture according to claim 22, wherein the enzyme is an ene reductase, the substrate is a compound comprising a carbon-carbon double bond and the co-factor is NAD.

26. The reaction mixture according to claim 22, wherein the enzyme is a transaminase, the substrate is a ketone and the co-factor is pyridoxal monophosphate.

27. The reaction mixture according to claim 1, wherein the concentration of the surfactant in the reaction mixture is at least 0.01% (w/w), at least 0.02% (w/w), at least 0.5% (w/w), or at least 1% (w/w).

28. The reaction mixture according to claim 1, wherein the concentration of the surfactant in the reaction mixture is in the range of 0.1% to 10% (w/w), 0.5% to 5% (w/w), 0.75% to 3% (w/w), or at about 2% (w/w).

29. The reaction mixture according to claim 1, wherein the enzyme is present in an amount in the range of 0.1% to 50%, 0.5% to 35%, or 1% to 20% of the amount of the substrate.

30. The reaction mixture according to claim 1, further comprising a buffer.

31. The reaction mixture according to claim 30, wherein the buffer is selected from the group consisting of TRIS, phosphate, citrate, acetate and ammonia.

32. The reaction mixture according to claim 1, wherein the reaction mixture has a pH value suitable for the enzymatic reaction.

33. The reaction mixture according to claim 32, wherein the pH value is in the range of from 4.0 to 10.0, from 6.0 to 8.0, from 6.5 to 7.5, or at about 7.0.

34. The reaction mixture according to claim 1, wherein the reaction mixture is of industrial scale.

35. The reaction mixture according to claim 34, wherein the volume of the reaction mixture is at least 10 L, at least 100 L, or at least 1000 L.

36. A method of performing an enzyme-catalyzed chemical synthesis reaction, comprising the steps of:
  (a) providing the reaction mixture as set forth in claim 1, and
  (b) performing the enzymatic reaction at a suitable pH and temperature.

37. The method according to claim 36, wherein the reaction is performed at a temperature of 80° C. or less.

38. The method according to claim 37, wherein the reaction is performed at a temperature in the range of 10° C. to 50° C., or 20° C. to 45° C.

39. The method according to claim 36, wherein the pH in the reaction mixture varies by at least 1.0, or at least 2.0 pH units during the reaction.

* * * * *